US005109338A

United States Patent [19]

Ermert et al.

[11] Patent Number: 5,109,338

[45] Date of Patent: Apr. 28, 1992

[54] HIGH-VOLTAGE GENERATOR AND METHOD FOR GENERATING A HIGH CURRENT, HIGH-VOLTAGE PULSE BY PULSE SHAPING FOR DRIVING A SHOCK WAVE SOURCE

[75] Inventors: Helmut Ermert, Roettenbach; Manfred Pfeiler, Erlangen, both of Fed. Rep. of Germany

[73] Assignee: Siemens Aktiengesellschaft, Berlin and Munich, Fed. Rep. of Germany

[21] Appl. No.: 407,113

[22] Filed: Sep. 14, 1989

[30] Foreign Application Priority Data

Sep. 23, 1988 [EP] European Pat. Off. ......... 88115714

[51] Int. Cl.[5] ...................... A61B 17/22; G06F 15/42

[52] U.S. Cl. .......................... 364/413.26; 128/24 EL; 606/128

[58] Field of Search ...................... 364/413.01, 413.26, 364/128, 328, 303, 24, 419, 660

[56] References Cited

U.S. PATENT DOCUMENTS 4,526,168 7/1985 Hassler et al. .

4,674,505 6/1987 Pauli et al. .

FOREIGN PATENT DOCUMENTS 2650624 5/1978 Fed. Rep. of Germany .

*Primary Examiner*—Gail O. Hayes

*Attorney, Agent, or Firm*—Hill, Van Santen, Steadman & Simpson

[57] ABSTRACT

A method and apparatus are disclosed for generating a high current, high-voltage pulse suitable for driving a shock wave source of the type which generates a shock wave in an acoustic transmission medium. In the apparatus, a signal generator generates a low-voltage signal having an energy content sufficient for generating the shock wave, and a pulse-shaping network, connected between the signal generator and the shock wave source, as a transfer function which shortens the signal duration of the low voltage signal from the signal generator so that the low-voltage signal is converted into a high voltage pulse suitable for driving the shock wave source. The high-voltage pulse has an energy content substantially the same as that of the low-voltage signal.

15 Claims, 1 Drawing Sheet

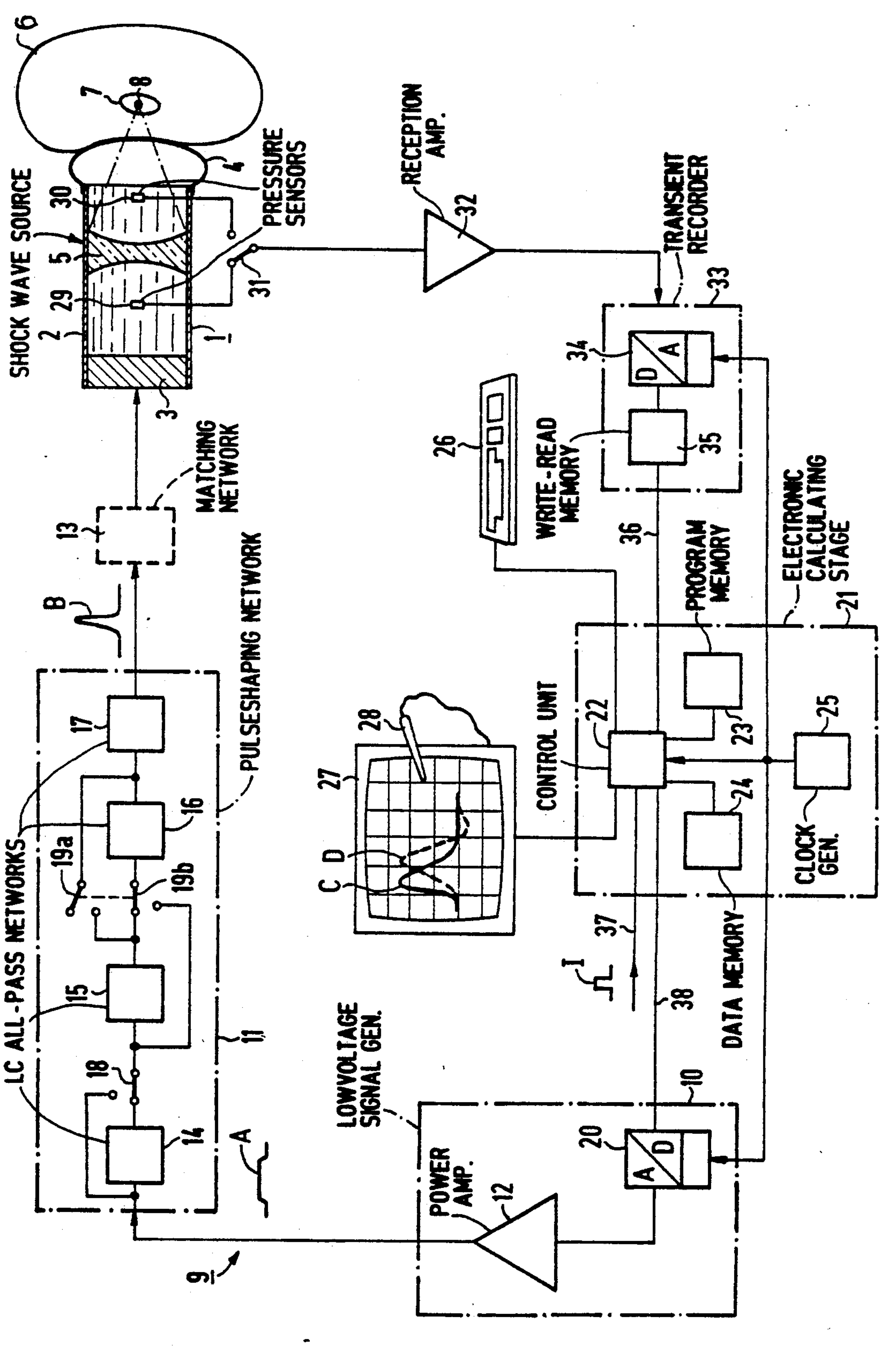
SHOCK WAVE SOURCE
PRESSURE SENSORS
RECEPTION AMP.
TRANSIENT RECORDER
MATCHING NETWORK
PULSESHAPING NETWORK
LC ALL-PASS NETWORKS
WRITE-READ MEMORY
PROGRAM MEMORY
ELECTRONIC CALCULATING STAGE
CONTROL UNIT
CLOCK GEN.
DATA MEMORY
LOWVOLTAGE SIGNAL GEN.
POWER AMP.

HIGH-VOLTAGE GENERATOR AND METHOD FOR GENERATING A HIGH CURRENT, HIGH-VOLTAGE PULSE BY PULSE SHAPING FOR DRIVING A SHOCK WAVE SOURCE

BACKGROUND OF THE INVENTION

1. Field of the Invention

The present invention is directed to a high-voltage generator for driving a shock wave source of the type which generates a shock wave in an acoustic transmission medium, as well as a method for generating a high-voltage, high current pulse.

2. Description of the Prior Art

Acoustic shock waves are used for a large variety of purposes, for example in materials research and in medical technology. In medical technology, shock waves are used for non-invasive treatment of stone maladies. The shock waves are focused on a calculus, for example a kidney stone, situated in the body of a patient and are coupled into the body of the patient and act upon the calculus to disintegrate the calculus into fragments of a size which can be eliminated (excreted) in a natural manner, or which can be dissolved with chemotherapeutic measures. It has also been suggested to treat malignant tissue, for example tumors, with shock waves.

Various types of shock wave sources are used for generating the shock waves, for example shock wave sources having an underwater spark gap, as described in German OS 26 50 624. It is also known to generate shock waves based on the electro-dynamic principle, as described in German OS 33 28 051, corresponding to U.S. Pat. No. 4,674,505. Shock waves can also be generated based on the piezoelectric principle, as described in German OS 33 19 871. All of these shock wave sources have in common the necessity of being supplied with a high-voltage pulse with high current in order to generate a shock wave. This type of pulse is usually generated with a high-voltage generator which contains a high-voltage capacitor chargeable to high-voltage, and a high-voltage switch, for example a triggerable spark gap switch. The high-voltage switch serves the purpose of connecting the charged high-voltage capacitor to the shock wave source, so that the electrical energy stored in the high-voltage capacitor suddenly discharges into the shock wave source, thereby generating a shock wave (see, for example, U.S. Pat. No. 4,674,505).

A disadvantage of these known shock wave sources is that the necessary high-voltage supply is expensive, and relatively susceptible to disruption. Additionally, the high-voltage switch can wear relatively quickly, and must then be replaced. Moreover, the wave shape (chronological amplitude curve and pulse duration) of the shock waves generated with the assistance of known high-voltage generators is difficult to adapt to the requirement of individual therapeutic cases. The capacitive, inductive and ohmic resistor components of the shock wave source form a network in common with the components of the high-voltage generator in which high-energy, pulse-like voltages and/or currents appear upon discharge of the high-voltage capacitor. Together with the acoustic properties of the shock wave source and the transmission medium (water or body tissue), the chronological curve of these voltages and currents determines the wave shape of the generated shock wave. Influencing the shape of the generated shock wave is thus only possible by modifying the electrical network formed by the high-voltage generator and the shock wave source, or by modifying the acoustic properties of the shock wave source. Both of these modifications are extremely complicated, and cannot be implemented in clinical practice. The wave shape of the generated shock wave therefore usually represents a compromise which cannot satisfy all possible therapeutic cases, namely those which have become routine, those which are under investigation in clinical research, and those which will arise in the future. Because the high-voltage supply provided for charging the high-voltage capacitor can only supply a relatively low charging current, the time required in the none high-voltage generators for charging the high-voltage capacitor is relatively long, and the maximum repetition rate of generating shock waves is correspondingly low.

The use of semiconductor components for forming the high-voltage switch is not possible, because semiconductor components cannot withstand the necessary high-voltages and high currents which occur during operation.

It is also known to drive the shock wave source with a generator constructed similar to an ultrasound transmitter. The shock wave source is chargeable with pulses having different chronological curves to adapt the wave shape of the shock wave to respective therapeutic cases. Such a system is described in German OS 31 19 295, corresponding to U.S. Pat. No. 4,526,168. This type of system, however, is only suitable for comparatively low-voltages and currents, which at most suffice for the drive of certain piezoelectric shock wave sources.

SUMMARY OF THE INVENTION

It is an object of the present invention to provide a high voltage generator capable of generating a high current, high-voltage pulse for driving a shock wave source, which does not require a high-voltage supply and high-voltage switches.

It is a further object of the present invention to provide such a high-voltage generator wherein the wave shape of the generated shock wave can be modified in a simple manner in combination with a shock wave source of an arbitrary type.

A further object of the invention is to provide a method for generating a high current, high-voltage pulse suitable for driving a shock wave source without the use of a high-voltage supply and high-voltage switches.

The above objects are achieved in a method and apparatus wherein a signal generator generates a low-voltage signal having an energy content sufficient for generating a shock wave, and wherein the low-voltage signal is supplied to a pulse-shaping network, connected between the signal generator and the shock wave source. The network has a transfer function which converts the incoming low-voltage signal into a high-voltage pulse suitable for driving a shock wave source. This is accomplished by shortening the pulse duration of the incoming signal, so that the resulting high-voltage, high current pulse has an energy content, i.e., area under the curve, which substantially corresponds to that of the incoming low-voltage signal. Thus the high-voltage pulse is not generated with the assistance of high-voltage switches, but instead is generated using a pulseshaping network constructed on passive, low-loss components, for example coils and capacitors. In contrast to known high-voltage voltage generators, a high-voltage supply is not required. In the invention, this is replaced by the signal generator which only generates low-voltage signals. Such a signal generator can be economically constructed in conventional technology.

Moreover, using only measures at the signal generator, the signal duration and/or the amplitude curve of the low-voltage signal can be easily modified, which thereby permits the shape of the resulting high-voltage pulse created by the pulse shaping network to be altered. This, in turn, significantly determines the shape of the generated shock wave, so that shock waves having differing wave shapes can be generated in a simple manner. Compared to known devices, the maximum repetition rate of the shock waves generated according to the method and apparatus disclosed herein is considerably increased, because the signal generator can supply the low signals with a high repetition rate.

The operation of the pulse shaping network is based on the fact that signals of arbitrary shape can be represented by superimposing harmonic oscillations of different frequencies. When a signal passes through a network having a transfer function which is selected so that different transit times through the network exist for different frequencies, a boost in the amplitude of the signal, given a simultaneous reduction of the signal duration, is achieved as a consequence of the different transit times of the individual frequency components of the low-voltage signal. In this manner, the low-voltage signal is converted into a high-voltage pulse in a simple manner in the pulse shaping network, with the pulse duration of the high-voltage pulse at the output being significantly shorter than the signal duration of the low-voltage signal at the input of the network. Since the network is constructed of low-loss components, not only the bandwidth of the low-voltage signal is preserved, but also the energy content of the low-voltage signal is preserved. The high-voltage generator can cooperate with shock wave source of arbitrary types which require to be driven by high-voltage pulses.

Pulse shaping networks having a transfer function such that a signal supplied to the network input is converted into a high amplitude pulse while shortening its signal duration are known in the pulse-compression radar technology.

In one embodiment of the invention, the pulse shaping network is formed by a multi-stage filter formed by LC-all-pass networks. Such a filter can be constructed using capacitors and inductances which are stable under high-voltage conditions in a simple manner and is substantially loss-free.

In a further embodiment, the network may have a switchable transfer function, which can easily be achieved by providing switchable connections between the components of the pulse-shaping network. Switching the transfer function permits the wave shape to be modified while using the same low-voltage signal, because the shock wave source can be supplied with different high-voltage pulses depending upon the selected transfer function.

In a further embodiment, the signal generator may be provided with means for varying the signal duration and/or signal amplitude of the low-voltage signal, thereby providing further modifications in the characteristics of the generated shock wave.

Because the signal generator is a low-voltage circuit, there are no special difficulties in constructing the generator. In an preferred embodiment, having an especially simple configuration, the signal generator includes a digital-to-analog converter and an electronic calculating stage which supplies the digital-to-analog converter with a chronological sequence of amplitude values corresponding to the signal duration and to the amplitude curve of the low-voltage signal. The digital-to-analog converter converts this signal into the low-voltage signal. By varying the chronological sequence of amplitude values, low-voltage signals having an arbitrary signal shape can be achieved within the limits established by the resolution and conversion time of the digital-to-analog converter. A chronological sequence of amplitude values adapted to a particular treatment can be calculated in the calculating stage, and the chronological sequence can be stored in a memory of the calculating stage. The appropriate values from the memory can then be supplied to the digital-to-analog converter each time a shock wave is to be generated. It is also possible to store a plurality of prescribed, chronological sequences of amplitude values in the memory, and to supply these values to the digital-to-analog converter as needed, with each sequence corresponding to a specific wave shape of the generated shock wave.

The calculating stage can be formed by a clock generator, a function memory in which one or more chronological sequences of the amplitude values are stored, and by an addressing stage for the memory. The clock generator controls both the digital-to-analog and the addressing stage so that only a defined region of the memory is addressable, and the chronological sequence of amplitude values corresponding to a desired wave shape is stored in this region. In another embodiment of the invention, the electronic calculating stage calculates, proceeding from a defined, desired wave shape of the shock wave, a chronological sequence of amplitude values corresponding to the low voltage signal. This calculation takes the transfer function of the pulse-shaping network, the electro-acoustic properties of the shock wave source, and the acoustic properties of the transmission medium into consideration. Using a data input stage, for example a display with a light pen, the physician can draw a desired shock wave shape adapted to a particular treatment, and this wave shape can then automatically be generated.

In order to be able to check the extent to which the wave shape of a generated shock wave corresponds to the desired wave shape, a further embodiment of the invention provides a broadband, linear pressure sensor disposed in the transmission medium. This pressure sensor supplies a signal corresponding to the wave shape of the generated shock wave to an analog-to-digital converter. The analog-to-digital converter generates a chronological sequence of amplitude values corresponding to the wave shape of the generated shock wave, which can be supplied to the electronic calculating stage. In the calculating stage, a comparison of the generated wave shape to the desired wave shape is undertaken, and the results of the comparison are generated as an output in a form which permits the physician to determine the degree of correlation. The electronic calculating stage may also, based on the result of the comparison, undertake a correction of the chronological sequence of amplitude values supplied to the digital to analog converter in the event of deviations of the wave shape of the generated shock wave from the desired wave shape. Deviations of the generated wave shape from the desired wave shape which are caused, for example, by non-linear acoustic transmission characteristics of the transmission medium, are thus automatically eliminated.

In another embodiment of the invention, a clock generator is provided which generates clock pulses for the calculating stage, the digital to analog converter and the analog-to-digital converter. These components are thus synchronized, so that an exact designation of the transit times in the system formed by the combination of the high-voltage generator and the shock wave source is possible. This is of particular significance when non-linear acoustic transmission properties of the transmission medium are to be corrected.

If required, a further embodiment of the invention includes a substantially loss-free matching network connected between the pulse-shaping network and the shock wave source. The matching network achieves a broadband impedance matching of the pulse-shaping network to the shock wave source, to avoid efficiency-reducing reflections of the high-voltage pulse at the input of the shock wave source.

The above objects are also achieved in a method for generating a high-voltage pulse with a high current, suitable for driving a shock wave source, wherein the duration of a low-voltage signal, having an energy contents efficient for generating a shock wave, is shortened and converted into a high-voltage pulse suitable for driving the shock wave source. The energy content of the high-voltage pulse substantially corresponds to that of the low-voltage signal. This method can be executed without a high-voltage supply and without high-voltage switches. The method also includes the step of converting the low-voltage signal into a high-voltage pulse using a pulse-shaping network, so that the duration and amplitude curve of the low-voltage signal, proceeding from a defined shock wave shape, can be selected based on a consideration of the transfer function of the pulse-shaping network, the electro-acoustic properties of the shock wave source and the acoustic properties of the acoustic transmission medium. The high-voltage pulse drives the shock wave source to generate a shock wave having the desired wave shape. In this method, therefore, a low-voltage signal having a freely selectable time curve, high energy, long signal duration and low instantaneous power is generated, and is converted in the pulse-shaping network into a high-voltage pulse having approximately the same energy, shorter signal duration and high instantaneous power. The chronological curve of the instantaneous amplitudes of the low-voltage signal can be calculated so that the resulting high-voltage pulse drives the shock wave source to generate a shock wave optimized according to defined criteria.

DESCRIPTION OF THE DRAWINGS

The single figure is a schematic block diagram of a high-voltage generator constructed and operating in accordance with the principles of the present invention connected for use in a lithotripsy system.

DESCRIPTION OF THE PREFERRED EMBODIMENTS

A high-voltage generator in accordance with the principles of the present invention is shown in the figure for use in medical technology for disintegrating calculi in the body of a patient. The lithotripsy system includes a shock wave source 1 which may be as disclosed, for example, in the aforementioned U.S. Pat. No. 4,674,505. The shock wave source 1 has a tubular housing 2 filled with an acoustic transmission medium, such as water. One end of the housing 2 is provided with an electrodynamic shock wave generator 3, and its opposite end is closed by a flexible sack 4. An acoustic collecting lens 5 is disposed in the housing 2 between the shock wave generator 3 and the sack 4. The lens 5 focuses the planar shock waves generated by the shock wave generator 3 so that they converge at the focus of the lens 5.

The shock wave source 1 is pressed against the body 6 (shown in cross-section) of a patient so that the sack 4 is in contact with the skin of the patient. The shock wave source 1 and the patient 6 are relatively positioned so that a calculus 8, such as a kidney stone situated in a kidney 7 of the patient, is located in the focus of the collecting lens 5. The focussed shock waves from the shock wave source 1 propagate in the body tissue of the patient, which functions as an acoustic transmission medium, and act upon the calculus 8 by exerting mechanical stresses thereon, thereby causing the calculus 8 to disintegrate into small fragments which can be eliminated naturally or with chemotherapeutic assistance.

A high-voltage generated constructed and operating in accordance with the principles of the present invention is generally referenced 9, and is provided for driving the shock wave source 1. As described below, the high-voltage generator 9 generates high-voltage, high current pulses suitable for generating a shock wave in the shock wave source 1.

The high-voltage generator 9 includes a low-voltage signal generator 10 and a pulse-shaping network 11. The low-voltage signal generator 10 generates a low-voltage output signal having a low amplitude (1 through 20 volts for example) and a relatively long signal duration. Such a low-voltage signal is indicated at A, as an example. The signal a is supplied at the output of a power amplifier 12 in the signal generator 10, and forms the input of the pulse-shaping network 11. The pulse shaping network 11 has a transfer function which, by shortening the duration of the low-voltage signal A received from the signal generator 10, converts this input signal into a high-voltage output pulse suitable for generating a shock wave. The energy content of the output pulse is substantially the same as the energy content of the low-voltage signal A. The high-voltage pulse appears at the output of the network 11, and is schematically indicated at B. This pulse is supplied to the shock wave source 1 for generating a shock wave. If necessary, a matching network 13, indicated in dashed lines in the figure, can be connected between the output of the pulse shaping network 11 and the shock wave source 1 for loss-free, broadband impedance matching of the output of the network 11 to the shock wave source 1.

In the embodiment shown in the figure, the pulse shaping network 11 is a multi-stage filter formed by a series of LC-all-pass networks 14, 15, 16 and 17. The multi-stage filter formed by the networks 14–17 has a transfer function such that individual frequency components contained in the low-voltage signal A have different transit times through the multi-stage filter so that the pulse duration of the low-voltage signal A is shortened, and the amplitude of the low-voltage signal A is boosted into the high-voltage region. The all-pass networks 14–17 consist of substantially loss-free components, so that the high-voltage pulse B at the output of the network 11 exhibits substantially the same energy content as the low-voltage signal A. To vary the transfer function of the pulse shaping network 11, and thus to generate shock waves having differing wave shapes, the individual all-pass networks can be selectively bridged (bypassed) such as by the operation of the switch 18 following the network 14.

There is also the possibility of connecting certain of the all-pass networks in parallel or in series as is possible, for example, for the all-pass networks 15 and 16 by the operation of ganged switches 19*a* and 19*b*.

A further possibility for influencing the wave shape of the generated shock wave is to supply the pulse shaping network 10 with low-voltage signals A having different chronological curves. For this purpose, the signal generator 10 is constructed so that the signal duration and/or amplitude curve of the generated low-voltage signal A are adjustable. In the embodiment shown in the drawing, this is achieved by a digital-to-analog converter 20 in the signal generator 10, to which a chronological sequence of amplitude values, corresponding to the pulse duration and to the amplitude curve of a low-voltage signal A, is supplied. The digital-to-analog converter 20 converts these amplitude values into the low voltage signal A. The digital-to-analog converter 20 of the signal generator 10 receives the chronological sequence amplitude values via a data bus 38 (of which only one line is shown). The opposite end of the data bus 38 is connected to an electronic calculating stage 21 in which a plurality of chronological sequences of amplitude values, corresponding to different wave shapes of the shock wave, are stored.

The electronic calculating stage 21 includes a central control unit 22, a program memory which contains the required programs for the functions of the high-voltage generator 9 as set forth below, a data memory 24 in which the chronological sequences of amplitude values corresponding to different shapes of shock waves are stored, and a clock generator 25. A keyboard 26 and a data display 27 with a light pen 28 are connected to the calculating stage 21. By suitable actuation of the keyboard 26, the calculating stage 21 can be initialized to call the chronological sequence of amplitude values from the data memory 24 corresponding to the desired wave shape. This sequence is supplied to the signal generator 10 for generating the associated low-voltage signal A each time a shock wave is to generated. There is thus the possibility of graphically portraying the respective wave shape of the shock wave on the display 27. The electronic calculating stage 21 and the signal generator 10, including the power amplifier 12, thus in combination constitute a wave shape generator, with which low-voltage signals A having an arbitrary signal shape can be generated, within the limits set by the amplitude resolution and by the conversion time of the digital-to-analog converter 20. The electronic calculating stage 21 essentially acts as a function memory in this operating mode, and supplies the required clock pulses to the digital-to-analog converter 20 from the clock generator 25.

By suitable actuation of the keyboard 26, or by drawing on the screen of the data display 27 with the light pen 28, a desired wave shape of the shock wave can be prescribed. Based on the prescribed, desired wave shape of the shock wave, the electronic calculating means 21 calculates the chronological sequence of amplitude values of a low-voltage signal A which is suitable for generating a shock wave having the desired shape. In making this calculation, the calculating stage 21 takes into the account the transfer function of the pulse shaping network 11, the electro-acoustic properties of the shock wave source 1, and the acoustic properties of the transmission medium. Data regarding all of these factors are stored in the data memory 24. The chronological sequence of amplitude values is also stored in the data memory 24, and is supplied to the digital-to-analog converter 20 of the signal generator 10 each time a shock wave is to be generated. A wave shape of the shock wave can thus be achieved which is optimally adapted to a particular therapy.

Additionally, the high-voltage generator 9 of the invention offers the possibility of checking to what extent the wave shape of the generated shock wave coincides with the prescribed desired wave shape. For this purpose, two linear broadband pressure sensors 29 and 30 are disposed in the transmission medium in the shock wave source 1. One of these pressure sensors precedes the acoustic collecting lens 5 and the other follows the lens 5. The pressure sensors 29 and 30 which are connectible one at a time to a reception amplifier 32 via a switch 31 supply electrical signals which correspond to the wave shape of the generated shock wave. The output of the reception amplifier 32 is connected to the input of a transient recorder 33, which includes an analog-to-digital converter 34 and a write-read memory 35. The signals of the pressure sensor 29 or 30 supplied to the analog-to-digital converter 34 are converted into a chronological sequence of amplitude values by the converter 34 (which receives its clock pulses from the clock generator 25 of the calculating stage 21). This chronological sequence of amplitude values is stored in the write-read memory 35. The write-read memory 35 is addressed with the electronic calculating stage 21 via a data/address bus 36, of which only a single line is shown. In response to a suitable actuation of the keyboard 26, the calculating stage 21 reads the chronological sequence of amplitude values stored in the write-read memory 35 which corresponds to the wave shape of the generated shock wave, and then undertakes a comparison of the desired wave shape therewith. The result of the comparison is portrayed on the display 27, such as graphically. This is shown in the drawing by a desired wave shape C (shown as a solid line) drawn, for example, with the light pen 28 on the screen of the display 27, and by a wave shape D (in dashed lines) of the generated shock wave, also on the screen of the display 27. The attending physician can decide on the basis of the illustrated display of the comparison as to whether the generated shock wave sufficiently coincides with the desired wave shape, or whether corrections are needed.

If a correction is determined to be necessary, the electronic calculating stage 21 proceeding from the result of the comparison and in response to a suitable actuation of the keyboard 26, undertakes a correction of the chronological sequence of amplitude values to be supplied to the digital-to-analog converter 20. This correction is made on the basis of the transfer function of the pulse-shaping network 11, the electro-acoustic properties of the shock wave source, and the acoustic properties of the transmission medium. The high-voltage generator 9 can thereby act as a "learning system") in that the calculating stage 21 evaluates the results of corrections which have been undertaken, and develops a correction strategy. In this context, it is important that the clock signals for the calculating stage 21, the digital-to-analog 20 and the analog-to-digital converter 34 are derived from the same clock generator 25, so that those components are synchronized. This permits an exact determination of the transit times of the signals in the system formed by the high-voltage generator 9 and the shock wave source 1, so that non-linear acoustic transmission properties of the transmission medium can be investigated and corrected.

As stated above, the calculating stage 21 is capable of repeatedly supplying the signal generator 10 with the respective chronological sequences of amplitude values, so that a sequence of shock waves can be generated. There is also the possibility of conducting trigger pulses I to the electronic calculating stage 21 via a line 37. These trigger pulses I are derived (in a manner not shown) from a periodic body function of the patient, for example the respiratory activity of the patient. The calculating stage 21 supplies the chronological sequence of amplitude values to the signal generator 10 upon the arrival of a trigger pulse I, so that the generation of shock waves ensues synchronously with the periodic body function which is being monitored.

A further advantage of the high-voltage generator 9 is that, in contrast to known devices, neither a high-voltage supply nor high-voltage switches are required. A further advantage is that shock waves having an arbitrary wave shape can be generated, and the wave shape of the shock waves can be optimized for a particular treatment. Because the low-voltage signal A generated by the signal generator 10 can be varied in fine time and amplitude steps using the calculating stage 21, the system has the capability of compensating linear distortions in the transmission behavior of the power amplifier 12, the matching network 13 (if used) and the shock wave source 1. Tolerances of the pulse-shaping network 11 when generating the low-voltage signals A can also be compensated. The transmission chain formed by the signal generator 10 (including the power amplifier 12), the pulse shaping network 11 and the matching network 13 (if used) acts as an inverse filter which effects a maximum compression of the low-voltage signals generated by the signal generator 10, with this transmission chain having an electrical input, which is the input of the power amplifier 12, and an acoustic output, which is the acoustic field generated by the shock wave source 1. Using the wave shapes of the generated shock waves identified with the pressure sensors 29 and 30 and with the transient recorder 33, the wave shapes can be optimized to achieve specific therapy results by using the electronic calculating stage 21. This insures that the therapy will have an optimum effect, and cavitation phenomena in the tissue of the patient receiving the treatment are suppressed, and the pain experienced by the patient during treatment is reduced.

Moreover, electro-acoustic properties of the shock wave generator 3, acoustic properties of the transmission medium, and electrical properties of the high-voltage generator 9 which unfavorably influence the shock wave generation can be substantially compensated.

Although modifications and changes may be suggested by those skilled in the art, it is the intention of the inventors to embody within the patent warranted hereon all changes and modifications as reasonably and properly come within the scope of their contribution to the art.

We claim as our invention:

1. A high-voltage generator for generating a high-voltage, high current pulse for driving a shock wave source, said shock wave source generating a shock wave in an acoustic transmission medium from said pulse, said high-voltage generator comprising:

signal generator means for generating a low-voltage signal having an energy content sufficient for generating a shock wave; and a pulse-shaping means connected to an output of said signal generator means and adapted for connection to said shock wave source and having a transfer function for shortening a signal duration of said low-voltage signal and for converting said low-voltage signal into a high-voltage pulse adapted for-driving a shock wave source, said high-voltage pulse having an energy content substantially the same as the energy content of said low-voltage signal.

2. A high-voltage generator as claimed in claim 1, wherein said pulse shaping means is a multi-stage filter formed by a plurality of interconnected LC-all-pass networks.

3. A high-voltage generator as claimed in claim 1, wherein said pulse-shaping means includes a plurality of components, and wherein said pulse-shaping means has a plurality of states corresponding to respectively different configurations of said components with each state thereby giving said pulse-shaping network a different transfer function, and said pulse-shaping network further comprising means for switching among said different states for switching the transfer function of said pulse shaping network.

4. A high-voltage generator as claimed in claim 1, wherein said signal generator means includes means for varying the duration of said low-voltage signal.

5. A high-voltage generator as claimed in claim 1, wherein said signal generator means includes means for varying the amplitude curve of said low-voltage signal.

6. A high-voltage generator as claimed in claim further comprising:

a digital-to-analog converter in said signal generator means; and electronic calculating means for supplying a chronological sequence of amplitude values corresponding to different signal durations and amplitude curves of said low-voltage signal to said digital-to-analog converter, said digital-to-analog converter converting said chronological sequence into said low-voltage signal.

7. A high-voltage generator as claimed in claim 6, further comprising:

means for entering data into said electronic calculating means identifying a desired wave shape of said shock wave, the transfer function of said pulse shaping means, the electro-acoustic properties of said shock wave source, and the acoustic properties of said transmission medium, and wherein said electronic calculating means includes means for calculating said chronological sequence of amplitude values based on said desired wave shape of said shock wave, said transfer function of said pulse shaping means said electroacoustic properties of said shock wave source, and said acoustic properties of said transmission medium.

8. A high-voltage generator as claimed in claim 7, further comprising:

broadband, linear pressure sensor means adapted to be disposed in said transmission medium for generating a signal corresponding to the wave shape of the shock wave generated by said shock wave source;

an analog-to-digital converter connected to an output of said pressure sensor means, said analog-to-digital converter generating a chronological sequence of amplitude values corresponding to the wave shape of the generated shock wave based on the signals from said pressure sensor means;

means in said means for calculating for comparing said sequence of amplitude values corresponding to the wave shape from the analog-to-digital converter with said data corresponding to said desired wave shape; and means for displaying a result of the comparison of the generated wave shape with the desired wave shape.

9. A high-voltage generator as claimed in claim 8, further comprising:

means in said means for calculating to which said result of said comparison in supplied for correcting said chronological sequence of amplitude values as needed to substantially eliminate any deviations of said wave shape of said generated shock wave from said desired wave shape.

10. A high-voltage generator as claimed in claim 8, further comprising:

a clock generator connected to supply clock pulses to each of said means for calculating, said digital-to-converter and said analog-to-digital converter.

11. A high-voltage generator as claimed in claim 1, further comprising:

a substantially loss-free matching network connected to said output of said pulse shaping means and adapted for connection to a shock wave source for broadband, impedance matching of said pulse shaping means to said shock wave source.

12. A high-voltage generator adapted for use to drive a shock wave source to generate a series of shock waves in a transmission medium, said high-voltage generator comprising:

means for generating a low-voltage signal including means for varying the amplitude and duration of said low-voltage signal, said low-voltage signal having an energy content sufficient to generate a shock wave;

pulse-shaping means for converting said low-voltage signal into a high-voltage, high current pulse having substantially the same energy content as said low-voltage signal;

means for prescribing a desired wave shape of said shock wave; and calculating means connected to said means for prescribing a desired wave shape and to said means for varying the amplitude and duration of said low-voltage signal for supplying signals to said means for varying for generating a low-voltage signal which is converted into a high-voltage pulse which causes said shock wave source to generate a shock wave having said desired wave shape.

13. A high-voltage generator adapted for use to drive a shock wave source to generate a series of shock waves in a transmission medium, said high-voltage generator comprising:

means for generating a low-voltage signal including signal altering means for varying the amplitude and duration of said low-voltage signal, said low-voltage signal having an energy content sufficient to generate a shock wave;

pulse-shaping means for converting said low-voltage signal into a high-voltage, high current pulse having substantially the same energy content as said low-voltage signal;

means for prescribing a desired wave shape of said shock wave;

means adapted for interaction with said shock wave source for monitoring the actual wave shape of a shock wave generated by said shock wave source from a high-voltage pulse from said pulse shaping means; and means for comparing said desired wave shape with said actual wave shape and for generating signals supplied to said signal altering means for causing said signal altering means to vary said duration and amplitude of said low-voltage signal for generating, in combination with said pulse-shaping means, a high-voltage pulse adapted to generate a shock wave in said shock wave source having an actual wave shape substantially coinciding with said desired wave shape.

14. A method for generating a high-voltage, high current pulse for driving a shock wave source which generates a shock wave in an acoustic transmission medium, said method comprising the steps of:

generating a low-voltage signal having an energy content sufficient for generating a shock wave; and converting said low-voltage signal into a high-voltage, high current pulse by shortening the signal duration of said low-voltage signal while substantially preserving its energy content so that said high-voltage, high current pulse has substantially the same energy content as said low-voltage signal.

15. A method as claimed in claim 14, wherein the step of converting said low-voltage signal into said high-voltage, high current pulse is further defined by converting said low-voltage signal in a pulse-shaping network having a transfer function into said high-voltage, high current pulse, and comprising the additional steps of:

selecting a desired wave shape of said shock wave; and setting the signal duration and amplitude curve of said low-voltage signal based on said transfer function of said pulse shaping network, the electro-acoustic properties of the shock wave source and the acoustic properties of the acoustic transmission medium so that a low-voltage signal is generated which is converted into a high-voltage, high current pulse which causes the generation of a shock wave having a wave shape corresponding to said desired wave shape.

* * * * *